US00PP33644P2

(12) United States Plant Patent
Hartman

(10) Patent No.: US PP33,644 P2
(45) Date of Patent: Nov. 16, 2021

(54) ***CALADIUM* PLANT NAMED 'ARN BRZ OF14-40'**

(50) Latin Name: ***Caladium* X *hortulanum***
Varietal Denomination: ARN BRZ OF14-40

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/193,887

(22) Filed: Mar. 5, 2021

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'ARN BRZ OF14-40', characterized by its tall and upright to somewhat mounding plant habit; dense and bushy appearance; vigorous growth habit and moderate growth rate; fancy-type leaves that are pale green or pale greenish yellow in color and flushed with reddish bronze, with reddish bronze-colored margins, and midvein and primary veins that are greenish white tinged with reddish bronze in color surrounded by white areas; occasional dark green-colored flecks and/or blotches may be present; and petioles that are almost black in color with greenish or tan-colored stripes.

4 Drawing Sheets

Figure 1:
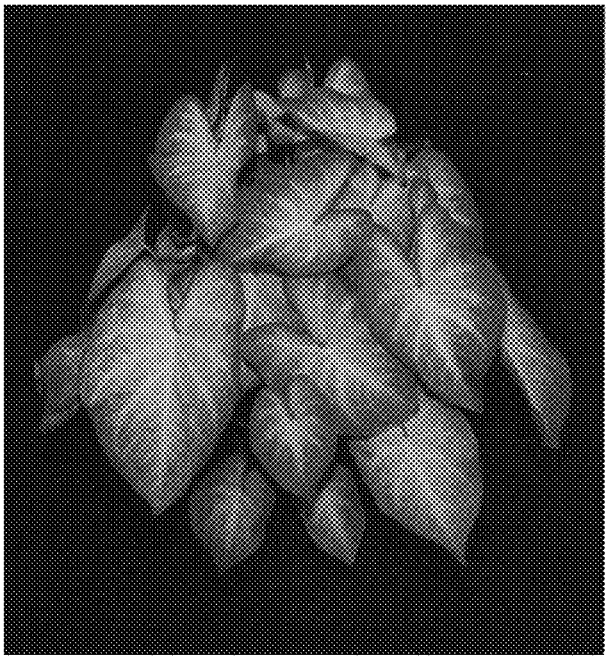

Botanical designation: *Caladium* X *hortulanum.*
Cultivar denomination: 'ARN BRZ OF14-40'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'ARN BRZ OF14-40'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'Twist N' Shout', not patented, as the female, or seed, parent with *Caladium* X *hortulanum* 'White Cap', disclosed in U.S. Plant Pat. No. 23,815, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ARN BRZ OF14-40'. These characteristics in combination distinguish 'ARN BRZ OF14-40' as a new and distinct *Caladium* plant:

1. Tall and upright to somewhat mounding plant habit; dense and bushy appearance.
2. Vigorous growth habit and moderate growth rate.
3. Fancy-type leaves that are pale green or pale greenish yellow in color and flushed with reddish bronze, with reddish bronze-colored margins, and midvein and primary veins that are greenish white tinged with reddish bronze in color surrounded by white areas; occasional dark green-colored flecks and/or blotches may be present.

4. Petioles that are almost black in color with greenish or tan-colored stripes.

Plants of the new *Caladium* differ primarily from plants of the female parent, 'Twist N' Shout', in the following characteristics:

1. Plants of the new *Caladium* are tall and upright whereas plants of 'Twist N' Shout' are intermediate to tall and upright.
2. Leaves of plants of the new *Caladium* are pale green or pale greenish yellow in color and flushed with reddish bronze, with reddish bronze-colored margins, and midvein and primary veins that are greenish white tinged with reddish bronze in color surrounded by white areas whereas leaves of 'Twist N' Shout' are olive green in color with green to coppery bronze-colored venation and coppery orange-colored spots and blotches.
3. Leaf petioles of plants of the new *Caladium* are almost black in color with greenish or tan-colored stripes whereas leaf petioles of plants of 'Twist N' Shout' are light green in color.

Plants of the new *Caladium* differ primarily from plants of the male parent, 'White Cap', in the following characteristics:

1. Plants of the new *Caladium* are tall and upright whereas plants of 'White Cap' are intermediate to tall and upright.
2. Leaves of plants of the new *Caladium* are pale green or pale greenish yellow in color and flushed with reddish bronze, with reddish bronze-colored margins, and midvein and primary veins that are greenish white tinged with reddish bronze in color surrounded by white areas whereas leaves of 'White Cap' have white-colored venation and white, greyed green and green speckled interveinal areas and dark green-colored margins.
3. Leaf petioles of plants of the new *Caladium* are almost black in color with greenish or tan-colored stripes whereas leaf petioles of plants of 'White Cap' are green in color with darker-colored stippling.

Plants of the new *Caladium* can be compared to plants of *Caladium* X *hortulanum* 'Aaron', not patented. In side-by-side comparisons, plants of the new *Caladium* differ primarily from plants of 'Aaron' in leaf color as leaves of the new *Caladium* are pale green or pale greenish yellow in color and flushed with reddish bronze, with reddish bronze-colored margins, and midvein and primary veins that are greenish white tinged with reddish bronze in color surrounded by white areas whereas leaves of 'Aaron' have white-colored venation and radiating interveinal areas surrounded with green-colored borders. In addition, plants of the new *Caladium* differ from plants of 'Aaron' in leaf petiole color as leaf petioles of plants of the new *Caladium* are almost black in color with greenish or tan-colored stripes whereas leaf petioles of plants of 'Aaron' are green in color.

Plants of the new *Caladium* can also be compared to plants of *Caladium* X *hortulanum* 'Water's Edge', disclosed in U.S. Plant Pat. No. 27,965. In side-by-side comparisons, plants of the new *Caladium* differ primarily from plants of 'Water's Edge' in leaf color as leaves of the new *Caladium* are pale green or pale greenish yellow in color and flushed with reddish bronze, with reddish bronze-colored margins, and midvein and primary veins that are greenish white tinged with reddish bronze in color surrounded by white areas whereas leaves of 'Water's Edge' have bright white-colored venation, grey green-colored interveinal areas surrounded by dark green borders. In addition, plants of the new *Caladium* differ from plants of 'Water's Edge' in leaf petiole color as leaf petioles of plants of the new *Caladium* are almost black in color with greenish or tan-colored stripes whereas leaf petioles of plants of 'Water's Edge' are green in color with dark brown-colored streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'ARN BRZ OF14-40' grown in a container that has had its tuber de-eyed prior to planting.

Figure 2:
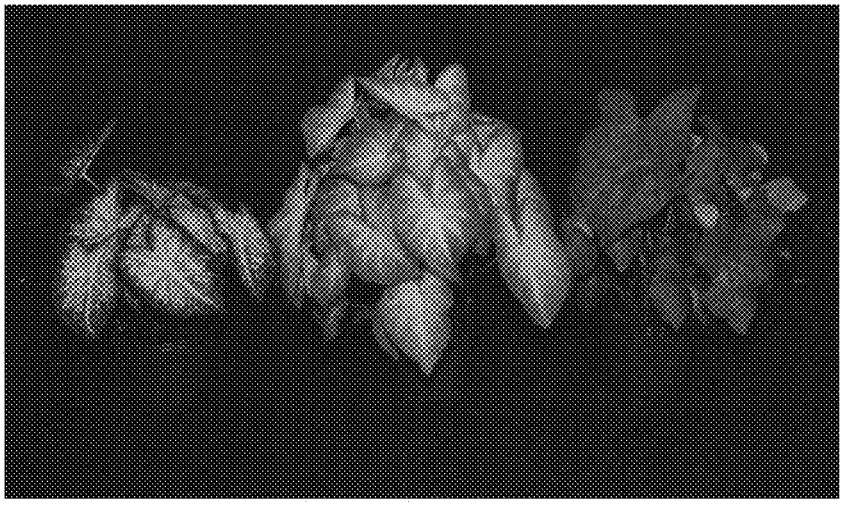

The photograph at the top of the second sheet (FIG. 2) is side perspective view of typical plants of the male parent, 'White Cap' (left), 'ARN BRZ OF14-40' (center) and the female parent, 'Twist N' Shout' (right).

Figure 3:
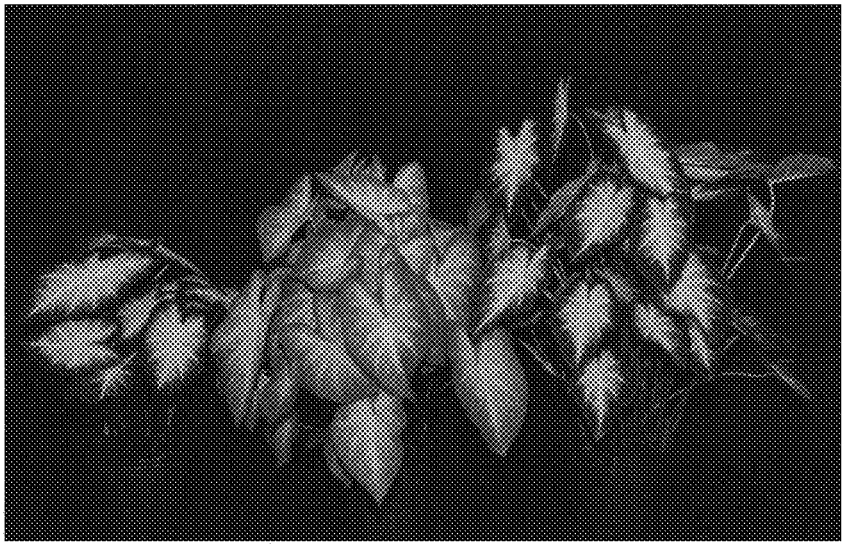

The photograph at the bottom of the second sheet (FIG. 3) is side perspective view of typical plants of 'Water's Edge' (left), 'ARN BRZ OF14-40' (center) and 'Aaron' (right).

Figure 4:
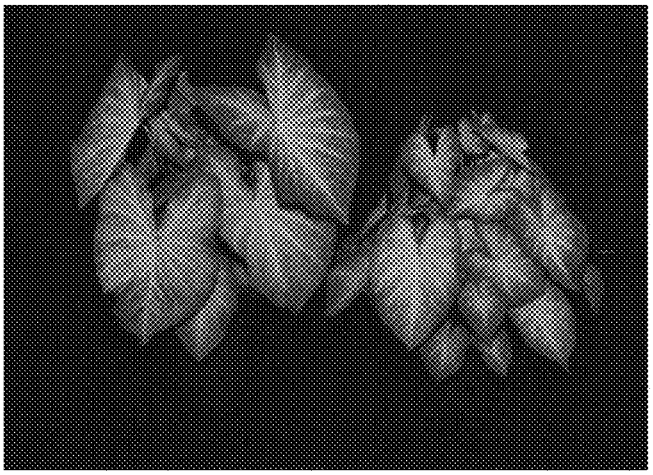

The photograph at the top of the third sheet (FIG. 4) is a comparison view of typical plants of 'ARN BRZ OF14-40' grown in containers, the plant on the left has not had its tuber de-eyed and the plant on the right has had its tuber de-eyed prior to planting.

Figure 5:
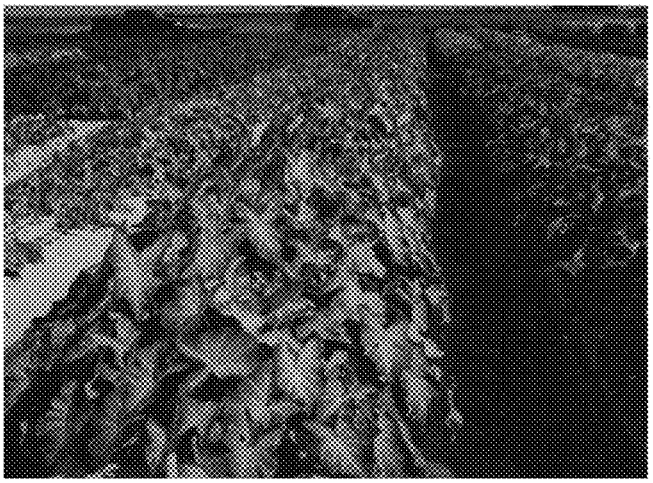

The photograph at the bottom of the third sheet (FIG. 5) is a side perspective view of typical plants of 'ARN BRZ OF14-40' grown in an open production field.

Figure 6:
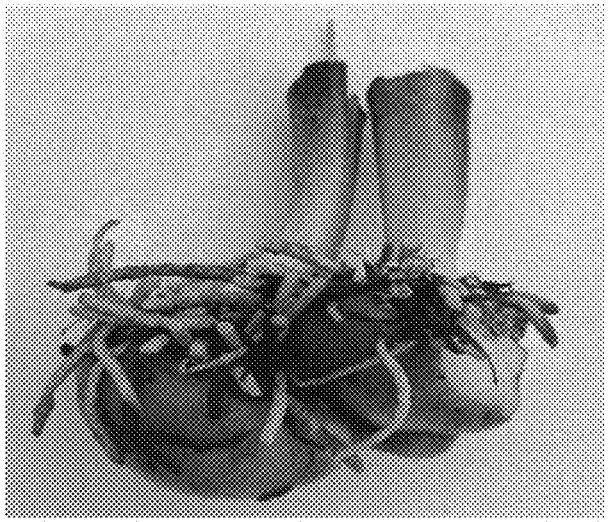

The photograph on the fourth sheet (FIG. 6) is a close-up view of typical freshly-harvested tubers with roots and leaf petioles of 'ARN BRZ OF14-40'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 750 μmol. During the production of the outdoor nursery-grown plants, day temperatures ranged from about 29° C. to 35° C., night temperatures ranged from about 23° C. to 26° C. and full sunlight conditions. Plants grown in the shade house were ten weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'ARN BRZ OF14-40'.

Parentage:

*Female, or seed, parent.*—*Caladium* X *hortulanum* 'Twist N' Shout' not patented.

*Male, or pollen, parent.*—*Caladium* X *hortulanum* 'White Cap', disclosed in U.S. Plant Pat. No. 23,815.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments are large and elliptic in shape. Height: About 3.3 cm to 4 cm. Diameter: About 6.5 cm to 8.8 cm. Segment height: About 3.4 cm. Segment diameter: About 6 cm. Axillary bud shape: Roughly triangular. Axillary bud size: About 5 mm by 6 mm. Texture: Thick, starchy; somewhat brittle. Color: Periderm, freshly-harvested: Close to N199B. Periderm, dried: Close to 200A. Epidermis: Close to N170D; when developing, close to 36D. Cortical tissue: Close to 155D. Axillary buds: Close to 36B and 36D. Root description: Thick, fleshy contractile roots with few lateral branches; color, close to NN155C. Rooting habit: Relatively sparse.

Plant description:

*Plant type.*—Herbaceous perennial; suitable as a potted plant in containers 15-cm to 25-cm and suitable as a landscape plant in shaded areas.

*Plant and growth habit.*—Tall and upright to somewhat mounding plant habit; dense and bushy appearance; vigorous growth habit and moderate growth rate; potted plants finish in saleable form in about six to seven weeks after planting tubers; leaf petioles and leaves arise from one or more growing points on tubers; leaf petioles initially upright and leaning outwardly with development.

*Plant height, from soil level to top of foliar plane, shade house-grown potted plants.*—When tubers are de-eyed, about 38.5 cm to 41 cm; tubers not de-eyed, about 46 cm to 47 cm.

*Plant diameter or spread, shade house-grown potted plants.*—When tubers are de-eyed, about 35 cm to 42 cm; tubers not de-eyed, about 35 cm to 49 cm.

*Number of shoots per plant, shade house-grown potted plants, tubers de-eyed.*—About two to four develop per #1 tuber.

*Number of shoots per plant, shade house-grown potted plants, tubers not de-eyed.*—About two to three develop per #1 tuber.

*Cataphylls, shade house-grown potted plants.*—Length: About 5.5 cm to 10.4 cm. Width: About 1.1 cm to 1.6 cm. Shape: Lanceolate. Apex: Acute to acuminate. Base: Sheathing the stein. Color, inner and outer surfaces: Close to N199C.

Leaf description:

*Arrangement and type.*—Alternate; simple; fancy-type.

*Length, shade house-grown potted plants, flattened.*—When tubers are de-eyed, about 15 cm to 19 cm; tubers not de-eyed, about 27 cm to 38 cm.

*Width, shade house-grown potted plants, flattened.*—When tubers are de-eyed, about 12 cm to 14.5 cm; tubers not de-eyed, about 18.5 cm to 26 cm.

*Shape.*—Ovate.

*Apex.*—Acute to acuminate.

*Base.*—Sagittate-peltate; cordate.

*Margin.*—Entire; mostly flat with broad undulations.

*Texture and luster, upper surface.*—Smooth, glabrous; dull sheen.

*Texture and luster, lower surface.*—Smooth, glabrous; slightly glaucous; dull sheen.

*Venation pattern.*—Pinnate and palmate.

*Color, shade house-grown potted plants.*—Fully developed leaves, upper surface: Interveinal areas: Variable, close to 193B, 157B, 157C, 150D, lighter than 148C, 148D, 176A to 176B and/or 175A tinged with close to 166A. Margins: Close to 176A to 176B or 148B flushed with close to 176A to 176B; edge, close to 187B to 187C. Basal notch: Close to 183C and 182D. Midvein: Close to 157C and 193D; distally, close to 157C and 193D flushed with close to 183D; areas surrounding midvein, close to NN155B, N155B or N155C flushed with close to 183D. Primary veins: Close to 195C to 195D variably flushed with close to 182B distally, flushed with close to 183D; areas surrounding primary venation, close to NN155B, N155B or N155C flushed with close to 183D. Occasionally, random flecks and/or blotches are observed: Close to 147A. Fully developed leaves, lower surface: Interveinal areas: Variable, close to 155B, 148D and/or 157B. Margins: Close to 147C; edge, close to 187B. Basal notch: Close to 183D and 187C. Midvein: Close to 145D; distally, close to 148D faintly tinged with close to 182D; areas surrounding midvein, close to NN155D. Primary veins: Close to 155C and 159D faintly and variably tinged with close to 182D; areas surrounding primary venation, close to NN155D.

*Petioles.*—Aspect: Initially upright and straight and leaning outwardly with development; flexible. Length, shade house-grown potted plants: When tubers are de-eyed, about 23 cm to 31 cm; tubers not de-eyed, about 26.5 cm to 38 cm. Diameter, distally, shade house-grown potted plants: When tubers are de-eyed, about 3 mm to 4 mm; tubers not de-eyed, about 5 mm to 6 mm. Diameter, proximally, shade house-grown potted plants: When tubers are de-eyed, about 6 mm to 8 mm; tubers not de-eyed, about 9 mm to 11 mm. Texture and luster: Smooth, glabrous; distally, glaucous; slightly glossy. Color, shade house-grown potted plants: Close to 203A to 203B variably striped with close to 147B to 147C or striped with close to N155C tinged with close to N170D; or close to N200A and N199A variably striped with close to N155B tinged with close to N170D; just below the leaf junction, close to 147D faintly and variably stippled, streaked and tessellated with close to 200A. Wing length, shade house-grown potted plants: About 7.2 cm to 8.4 cm. Wing diameter, shade house-grown potted plants: When tubers are de-eyed, about 7 mm; tubers not de-eyed, about 15 mm Texture and luster, inner and outer surfaces: Smooth, glabrous; slightly glossy. Wing color, shade house-grown potted plants: Outer surface: Close to 203A marbled with close to 147C to 147D; or close to 147C densely streaked, stippled and tessellated with close to N200A. Inner surface: Close to N155C tinged with close to 196D; colors and patterns on the outer surface are visible on the inner surface.

Inflorescence description: To date, inflorescence development has not been observed on plants of the new *Caladium*.

Pathogen tolerance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'ARN BRZ OF14-40' as illustrated and described.

* * * * *